United States Patent [19]

Trust et al.

[11] 4,242,515

[45] Dec. 30, 1980

[54] SUBSTITUTED 3-ALKYL-6-PHENYL-1,2,4-TRIAZOLO-[4,3-a]PYRIDINES

[75] Inventors: Ronald I. Trust, Monsey; Jay D. Albright, Nanuet, both of N.Y.

[73] Assignee: American Cyanamid Company, Stamford, Conn.

[21] Appl. No.: 24,849

[22] Filed: Mar. 28, 1979

[51] Int. Cl.³ .................... C07D 471/04; A61K 31/41
[52] U.S. Cl. .................................. 546/119; 546/120; 424/256
[58] Field of Search ................. 546/119, 120; 424/256

[56] References Cited

U.S. PATENT DOCUMENTS

| | | | |
|---|---|---|---|
| 2,913,454 | 11/1959 | Petersen et al. | 546/119 X |
| 3,050,525 | 8/1962 | Bicking | 546/119 |
| 3,597,423 | 8/1971 | Wiedemann et al. | 546/119 X |

FOREIGN PATENT DOCUMENTS 651682 11/1962 Canada ..................... 546/119

OTHER PUBLICATIONS

C.A., 79 (1973), Yurugi et al., 42417c.

Primary Examiner—Joseph Paul Brust
Attorney, Agent, or Firm—Edward A. Conroy, Jr.

[57] ABSTRACT

This disclosure describes novel 3-alkyl-6-(substituted-phenyl)-1,2,4-triazolo[4,3-a]pyridines useful as anxiolytic agents.

7 Claims, No Drawings

SUBSTITUTED 3-ALKYL-6-PHENYL-1,2,4-TRIAZOLO-[4,3-a] PYRIDINES

BRIEF SUMMARY OF THE INVENTION

This invention relates to new organic compounds and, more particularly, is concerned with novel 3-alkyl-6-(substituted-phenyl)-1,2,4-triazolo[4,3-a]pyridines which may be represented by the following structural formula:

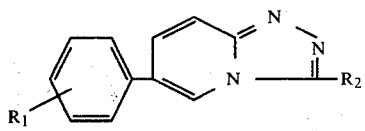

wherein $R_1$ is hydrogen, alkyl having from 1 to 4 carbon atoms, alkoxy having from 1 to 4 carbon atoms, fluoro, chloro, bromo, trifluoromethyl, cyano, carboxy, alkoxycarbonyl having from 2 to 5 carbon atoms, carboxamido, nitro, amino, acylamino having from 1 to 4 carbon atoms, monoalkylamino having from 1 to 4 carbon atoms or dialkylamino wherein each alkyl group has from 1 to 4 carbon atoms and they may be the same or different; and $R_2$ is alkyl having from 1 to 3 carbon atoms. The invention also includes novel compositions of matter containing the above-defined compounds which are useful for meliorating anxiety in mammals and the method of meliorating anxiety in mammals therewith. A preferred embodiment of the present invention may be represented by the above general formula wherein $R_1$ is in the meta-position and a most preferred embodiment may be represented by the above general formula wherein $R_1$ is m-methyl, m-methoxy, m-fluoro, m-chloro or m-trifluoromethyl.

DETAILED DESCRIPTION OF THE INVENTION

The novel compounds of the present invention are generally obtainable as white, tan, cream-colored or pale yellow crystalline solids having characteristic melting points and absorption spectra and which may be purified by recrystallization from common organic solvents such as methanol, ethanol, dimethylformamide, acetone, chloroform, ethyl acetate, methylene chloride, hexane, and the like or mixtures of these. They are appreciably soluble in non-polar organic solvents such as toluene and chloroform and the like, but are relatively insoluble in water. These compounds are organic bases and thus are capable of forming acid-addition salts, formed by admixture of the organic free base with up to two equivalents of an acid, suitably in a neutral solvent. Suitable salts are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The novel compounds of the present invention may be readily prepared as set forth in the following reaction scheme:

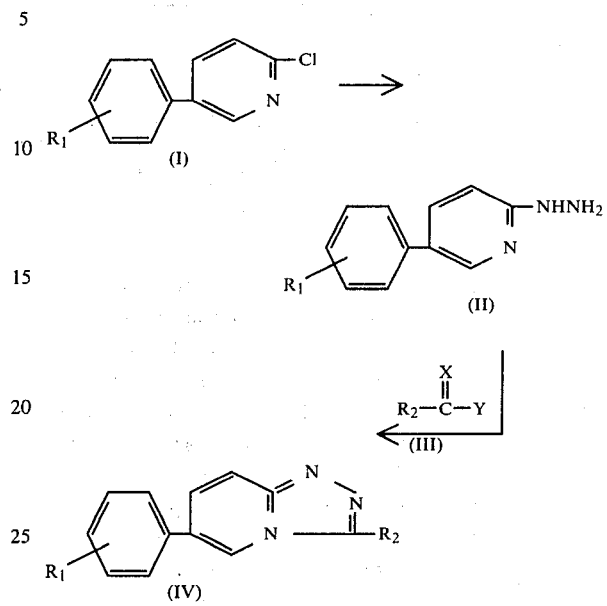

wherein $R_1$ and $R_2$ are as hereinabove defined and the groups X and Y in structure (III) above are taken together to be that functionality which is capable of reacting with the terminal amino group in structure (II) and cyclizing to give the cyclic products (IV). Examples of these structural types include: (1) a carboxylic acid where X is oxygen and Y is hydroxy, (2) an acid chloride where X is oxygen and Y is chloro, (3) an amide where X is oxygen and Y is $NH_2$, $NHR_3$ or $NR_3R_4$ wherein $R_3$ and $R_4$ are alkyl($C_1$–$C_4$), (4) an N,N-dialkylamide dialkylacetal where X is $(OR_5)_2$ and Y is $NR_3R_4$ wherein $R_3$, $R_4$ and $R_5$ are alkyl groups having up to 4 carbon atoms, (5) an ester where X is oxygen and Y is $OR_3$ wherein $R_3$ is as defined above, (6) an orthoester where X is $(OR_3)_2$ and Y is $OR_3$ wherein $R_3$ is as previously defined, and (7) an anhydride where X is oxygen and Y is $$\underset{R_2C-O}{\overset{O}{\|}}.$$

In accordance with the above reaction scheme, an appropriately substituted 2-chloro-5-phenylpyridine (I) is reacted with 95% hydrazine or hydrazine hydrate, which is preferably present in excess, at reflux temperature in pyridine or lower alkanol solvent for a period of 12-48 hours to provide the corresponding 2-hydrazino-5-phenylpyridine (II). Treatment of (II) with one of the above-described carbonyl insertion reagents (III) for a period of 1-24 hours at 50°-175° C. provides the corresponding 3-alkyl-6-phenyl-1,2,4-triazolo[4,3-a]pyridines ((IV) of the present invention. The reaction may be conducted with or without catalysis by bases such as pyridine or tri(lower alkyl)amines. The novel compounds of the present invention may also be readily prepared in accordance with the following reaction scheme:

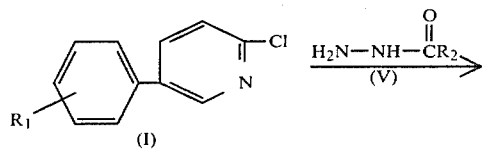

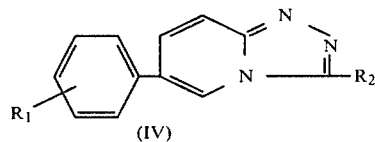

wherein $R_1$ and $R_2$ are as hereinabove defined. In accordance with the above reaction scheme, an appropriately substituted 2-chloro-5-phenylpyridine (I) is reacted with an acyl hydrazine of structure (V) in a lower alkanol or pyridine solvent at reflux temperature for a period of 12–48 hours to provide the corresponding 3-alkyl-6-phenyl-1,2,4-triazolo[4,3-a]pyridines (IV).

The appropriate 2-chloro-5-phenylpyridines (I) which are used as intermediates for the preparation of the compounds of the present invention may be prepared by any one of several convenient methods well-known in the art. In particular, the 2-chloro-5-phenylpyridines (I) may be conveniently prepared by one of the following synthetic routes:

First, the 2-chloro-5-phenylpyridines (I) may be prepared by diazotization of 2-chloro-5-aminopyridine (VII) in the presence of a phenyl derivative $R_1$–$C_6H_5$ (VI) according to J. Chem. Soc. 3181 (1949).

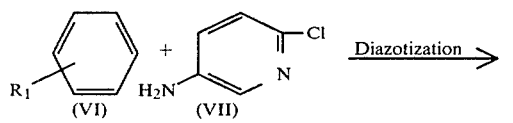

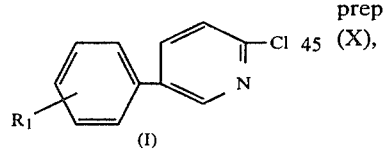

It is understood that in this reaction scheme successful formation of (I) will only be achieved if $R_1$ is a group capable of rendering the phenyl ring sufficiently reactive to undergo attack by the diazotized 2-chloro-5-amino pyridine (VII). Such $R_1$ groups are those which are considered activating or weakly deactivating toward Friedel-Crafts alkylation, (according to G. Olah in *Friedel Crafts and Related Reactions,* Interscience, New York 1963). It is also understood that if the above scheme is employed the $R_1 \neq$ hydrogen in structure (VI), then a mixture of isomeric products of structure (I) may be produced. However it is expected that an isomeric mixture of this type may be separable by any of a number of separation techniques familiar to those skilled in the art such as crystallization, distillation, sublimation, liquid chromatography, gas chromatography, or the like.

Second, the 2-chloro-5-phenylpyridines (I) may be preferably prepared in accordance with the following reaction scheme:

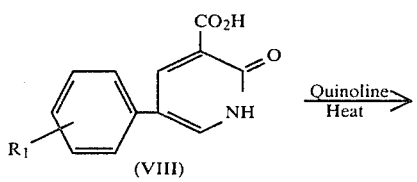

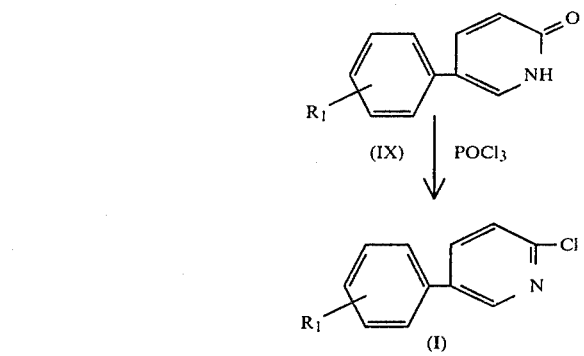

wherein $R_1$ is as hereinabove defined. In accordance with the above reaction scheme, an appropriately substituted 1,2-dihydro-2-oxo-5-phenyl-3-pyridinecarboxylic acid (VIII) is heated in quinoline at a temperature of 190°–235° C. for 4–24 hours in an inert atmosphere to produce the appropriately substituted 5-phenyl-2(1H)-pyridinone (IX). Treatment of (IX) with phosphorus oxychloride provides the substituted 2-chloro-5-phenylpyridine (I).

The substituted 1,2-dihydro-2-oxo-5-phenyl-3-pyridinecarboxylic acids (VIII) may be conveniently prepared by hydrolysis of a compound of the formula (X),

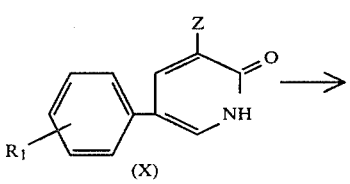

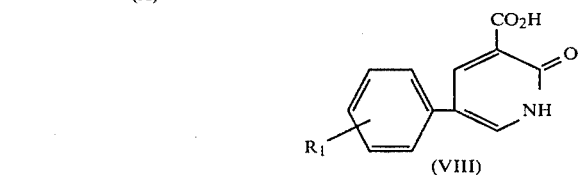

wherein $R_1$ is as hereinabove defined and Z is a group capable of being transformed into a carboxyl group by hydrolysis, such as cyano, alkoxycarbonyl, carbamoyl, thiocarbamoyl, or the like.

The compounds of formula (X) may be conveniently prepared according to the following scheme:

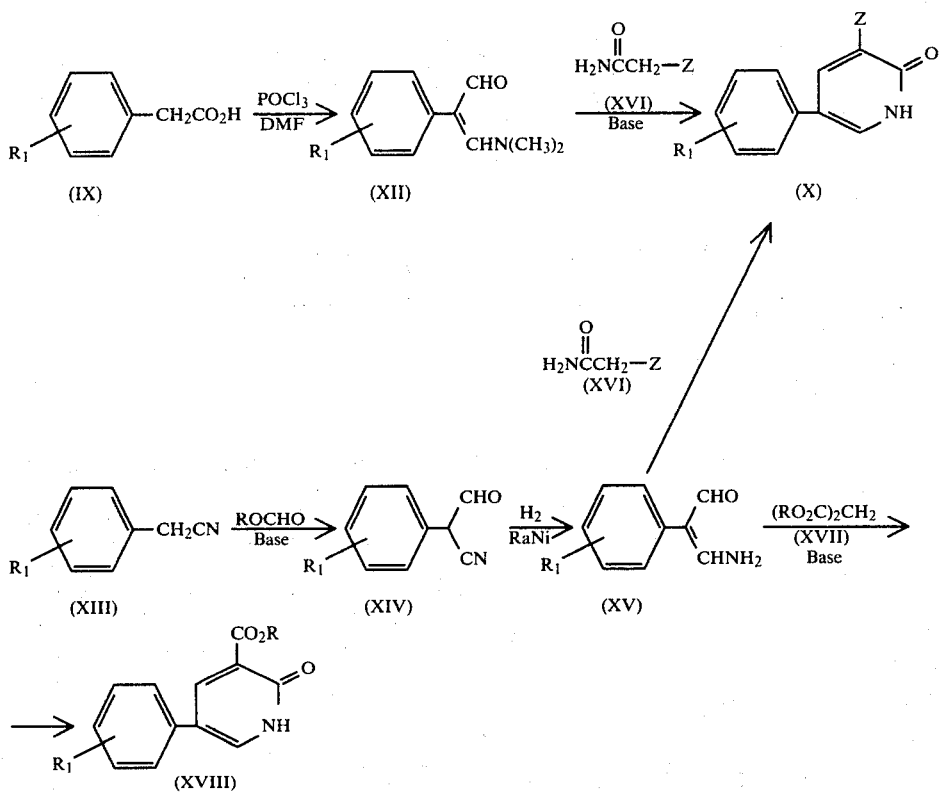

wherein $R_1$ and Z are as hereinabove defined and R is a lower alkyl group up to 4 carbon atoms. In accordance with the above scheme, the substituted 3-(dimethylamino)-2-phenyl-2-propenals (XII) may be condensed with an activated methylene compound of formula (XVI) with or without an alkali alkoxide catalyst such as sodium methoxide, sodium ethoxide or an organic base such as pyridine, piperidine or triethylamine to give the compounds of formula (X). Examples of active methylene compounds of formula (XVI) may be cyanoacetamide, malonamide, methyl malonomate, ethyl malonomate, malonamic acid or 2-(N,N-dimethylthiocarbamoyl)acetamide. These same active methylene derivatives of formula (XVI) may be condensed with the substituted 3-amino-2-phenyl-2-propenals of structure (XV) in an identical fashion to produce the compounds of formula (X). In addition, compounds (XV) may be condensed with dialkyl malonates such as dimethylmalonate or diethylmalonate to yield specifically the lower alkyl 1,2-dihydro-2-oxo-5-phenyl-3-pyridinecarboxylates (XVIII). The 3-(dimethylamino)-2-phenyl-2-propenals (XII) are conveniently prepared from an appropriately substituted phenyl acetic acid (XI) and dimethylformamide-phosphorus oxychloride. The 3-amino-2-phenyl-2-propenals (XV) are prepared from a substituted phenylacetonitrile by initial formylation with an alkyl formate and base followed by reduction with hydrogen using a Raney nickel catalyst. It is understood that while many of the 3-alkyl-6-phenyl-1,2,4-triazolo[4,3-a]pyridines of the present invention may be prepared by starting with either the substituted phenylacetic acids (XI) or the phenylacetonitriles (XIII) with equal facility, it may sometimes be preferable to select that procedure which is most compatible with the chemical properties of the substituent $R_1$.

It is also understood that certain members of the substituted 3-alkyl-6-phenyl-1,2,4-triazolo[4,3-a]pyridines as described in this invention may be preferably prepared from other substituted 3-alkyl-6-phenyl-1,2,4-triazolo[4,3-a]pyridines, instead of starting with a unique starting material, as shown in the following schemes:

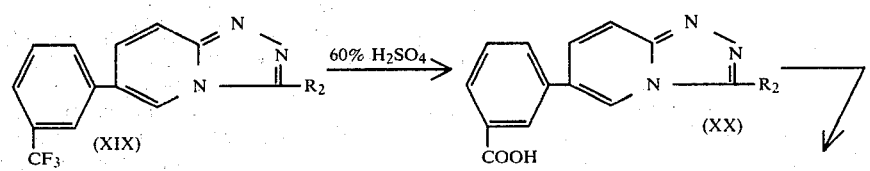

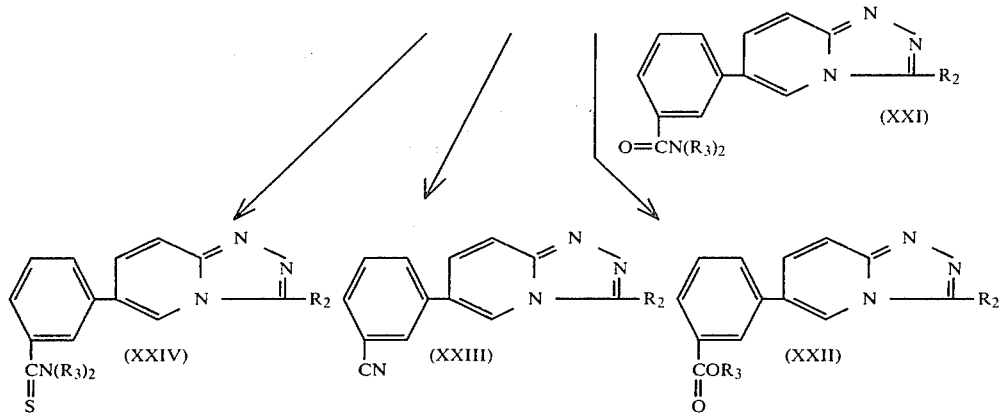

where $R_3$ is an alkyl group of up to 4 carbon atoms. In accordance with the above scheme, 3-methyl-6-[3-(trifluoromethyl)phenyl]-1,2,4-triazolo[4,3-a]pyridine (XIX) ($R_2=CH_3$) may be hydrolyzed to the carboxylic acid (XX), which may be in turn converted to the derivatives (XXI–XXIV) by standard methods. Also is noted the following transformations, which may be used to prepare other derivatives of this invention.

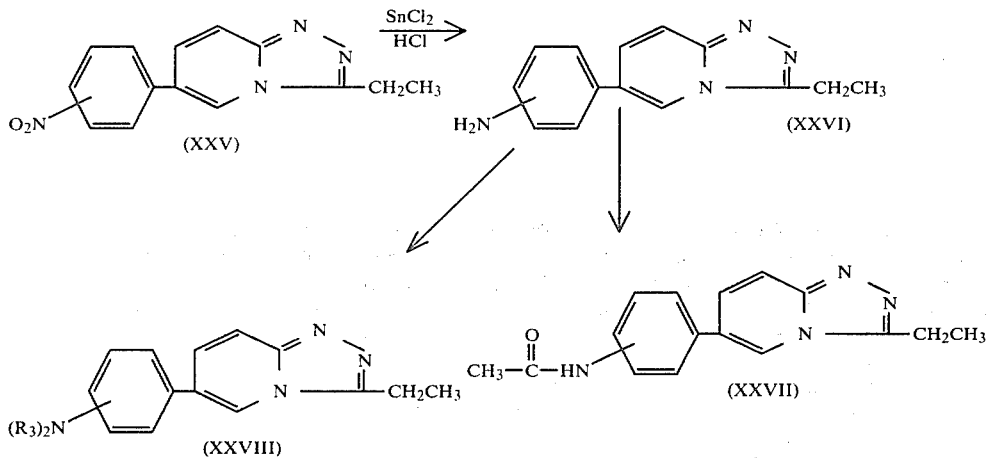

wherein $R_3$ is selected from an alkyl group of up to 4 carbon atoms and $R_3$ may be the same or different. In accordance with the above scheme, 3-ethyl-6-(4-nitrophenyl)-1,2,4-triazolo[4,3-a]pyridine (XXV) may be treated with an agent capable of reducing a nitro group, ie., stannous chloride in hydrochloric acid, to yield 3-ethyl-6-(4-aminophenyl)-1,2,4-triazolo[4,3-a]pyridine (XXVI), which may be transformed by standard methods to the derivatives (XXVII) and (XXVIII).

The novel compounds of the present invention possess central nervous system activity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. The following representative compounds of the present invention have been shown to possess anxiolytic activity when tested as described above.

6-Phenyl-3-methyl-1,2,4-triazolo[4,3-a]pyridine 6-(4-Chlorophenyl)-3-methyl-1,2,4-triazolo[4,3-a]pyridine 6-(3-Fluorophenyl)-3-methyl-1,2,4-triazolo[4,3-a]pyridine 6-[3-(Trifluoromethyl)phenyl]-3-methyl-1,2,4-triazolo[4,3-a]pyridine Another test which has been used to asses anti-anxiety effect is a non-conditioned passive avoidance procedure described by J. R. Vogel, B. Beer and D. E. Clody, "A Simple and Reliable Conflict Procedure for Testing Anti-Anxiety Agents", Psychopharmacologia, 21 1-7 (1971). A conflict situation is induced in rats by a modification of this method.

Groups of 6 naive, Wistar strain rats, weighing 200-240 g. each were deprived of water for 48 hours and food for 24 hours. The test compounds were administered in single or graded, oral or intraperitoneal, doses suspended in a 2% starch vehicle containing 0.5% v/v polyethylene glycol and one drop of polysorbate 80. Control animals received the vehicle alone. At 30 or 60 minutes, each rat was placed in individual black plexiglass chambers. A 10% dextrose solution was available ad libitum from a tap located in the rear of the chamber. A 0.3 milliampere constant 60 Hz pulsed DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the shocks received by the test group are significantly different from the control group by the Mann-Whitney U test. The following representative compounds of the present invention have been shown to possess anxiolytic activity when tested as described above.

6-(4-Chlorophenyl)-3-methyl-1,2,4-triazolo[4,3-a]pyridine
6-(3-Fluorophenyl)-3-methyl-1,2,4-triazolo[4,3-a]pyridine
6-(3-Trifluoromethyl)phenyl-3-methyl-1,2,4-triazolo[4,3-a]pyridine The novel compounds of the present invention have been found to be highly useful for meliorating anxiety in mammals when administered in amounts ranging from about 0.1 mg. to about 20.0 mg./kg. of body weight per day. A preferred dosage regimen for optimum results would be from about 0.5 mg. to about 10.0 mg./kg. of body weight per day. Such dosage units are employed that a total of from about 35 to about 700 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-$\alpha$-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

2-(4-Chlorophenyl)-3-(dimethylamino)-2-propenal

To a slurry of Vilsmeyer reagent, (formed from a stirred mixture of 92.0 g. of phosphorus oxychloride and 73.0 g. of N,N-dimethylformamide at a temperature below 10° C.) is added 34.12 g. of 4-chlorophenylacetic acid. This mixture is stirred at ambient temperature for 30 minutes, then is heated to 70°–80° C. during which time the mixture becomes effervescent. The mixture is kept at 70°–80° C. for 5.5 hours, then is allowed to cool. The cooled mixture is slowly poured onto cracked ice, and ice is added intermittently to maintain the temperature of the mixture below 15° C. during the portionwise addition of potassium carbonate and until pH 10 is achieved. Then 150 ml. of toluene is added and the mixture is heated on a steam bath for one hour. After cooling, the layers are separated and the aqueous layer is extracted with an additional 100 ml. of toluene. The organic layers are combined, copiously washed with water, dried over anhydrous sodium sulfate and evaporated at reduced pressure to yield a yellow solid. The solid is recrystallized from hexane to give 27.3 g. of the product of the Example as a tan solid, mp. 121°–124° C.

EXAMPLE 2

3-(Dimethylamino)-2-phenyl-2-propenal

In the manner described in Example 1, 91.12 g. of phenylacetic acid is reacted with Vilsmeyer reagent to yield 45.0 g. of the product of the Example as a yellow solid m.p. 48°–51° C.

EXAMPLE 3

3-(Dimethylamino)-2-(3-fluorophenyl)-2-propenal

In the manner described in Example 1, 102.5 g. of 3-fluorophenylacetic acid is reacted with Vilsmeyer reagent to provide 90.0 g. of the product of the Example as yellow prisms, m.p. 42°–43.5° C.

EXAMPLE 4

3-(Dimethylamino)-2-[3-(trifluoromethyl)phenyl]-2-propenal

In the manner described in Example 1, 123.0 g. of 3-(trifluoromethyl)phenylacetic acid is reacted with Vilsmeyer reagent to give 89.5 g. of the product of the Example as a tan solid, m.p. 128.5°–131.5° C.

EXAMPLE 5

2-(2-Chlorophenyl)-3-(dimethylamino)-2-propenal

In the manner described in Example 1, 126.5 g. of 2-chlorophenylacetic acid is reacted with Vilsmeyer reagent to yield 102.1 g. of the product of the Example as a yellow solid, m.p. 86.5°–88.5° C.

Additional compounds which may be prepared in a manner similar to that described for the preceding examples are:

3-(Dimethylamino)-2-(4-fluorophenyl)-2-propenal
3-(Dimethylamino)-2-(2-fluorophenyl)-2-propenal
2-(3-Chlorophenyl)-3-(dimethylamino)-2-propenal
2-(4-Bromophenyl)-3-(dimethylamino)-2-propenal
3-(Dimethylamino)-2-[2-(trifluoromethyl)phenyl]-2-propenal
3-(Dimethylamino)-2-(3-nitrophenyl)-2-propenal
3-(Dimethylamino)-2-(4-nitrophenyl)-2-propenal
3-(Dimethylamino)-2-(3-methylphenyl)-2-propenal

EXAMPLE 6

5-(4-Chlorophenyl)-1,2-dihydro-2-oxo-3-pyridinecarbonitrile

To a solution of 37.6 g. of sodium methoxide in 650 ml. of methanol is added 29.24 g. of cyanoacetamide followed by 26.1 g. of 2-(4-chlorophenyl)-3-(dimethylamino)-2-propenal. The resulting solution is heated at reflux temperature for 16 hours to separate a yellow solid. Then 50 ml. of glacial acetic acid is added and the mixture is diluted with water, causing a new yellow solid to separate. This solid is collected by filtration and is washed with water to give 60.5 g. of the product of the Example m.p. 285°–290° C.

EXAMPLE 7

1,2-Dihydro-5-(3-fluorophenyl)-2-oxo-3-pyridinecarbonitrile

In the manner described in Example 6, a solution of 41.6 g. of sodium methoxide and 32.3 g. of cyanoacetamide in 750 ml. of methanol is reacted with 74.2 g. of 3-(dimethylamino)-2-(3-fluorophenyl)-2-propenal to yield 62.0 g. of the product of the Example as a cream colored solid, m.p. 261°–266° C.

EXAMPLE 8

1,2-Dihydro-5-(3-methylphenyl)-2-oxo-3-pyridinecarbonitrile

In the manner described in Example 6, a solution of 13.7 g. of sodium methoxide and 10.7 g. of cyanoacetamide in 250 ml. of methanol and 24.0 g. of 3-(dimethylamino)-2-(3-methylphenyl)-2-propenal is refluxed overnight to give 12.0 g. of the product of the Example as a yellow solid, m.p. 254.5°–260° C.

EXAMPLE 9

1,2-Dihydro-2-oxo-5-phenyl-3-pyridinecarbonitrile

In the manner described in Example 6, a solution of 28.5 g. of sodium methoxide and 22.2 g. of cyanoacetamide in 500 ml. of methanol is heated at reflux for 16 hours with 42.0 g. of 3-(dimethylamino)-2-phenyl-2-propenal to yield 12.5 g. of the product of the Example as a yellow amorphous solid.

EXAMPLE 10

1,2-Dihydro-2-oxo-5-[3-(trifluoromethyl)phenyl]-3-pyridinecarbonitrile

In the manner described in Example 6, a solution of 36.7 g. of sodium methoxide and 28.2 g. of cyanoacetamide in 650 ml. of methanol is heated at reflux for 16 hours with 71.5 g. of 3-(dimethylamino)-2-[3-(trifluoromethyl)phenyl]-2-propenal to yield 61.8 g. of the product of the Example as colorless crystals, m.p. 242°–246° C.

EXAMPLE 11

5-(2-Chlorophenyl)-1,2-dihydro-2-oxo-3-pyridinecarbonitrile

In the manner described in Example 6, a solution of 48.6 g. of sodium methoxide and 42.0 g. of cyanoacetamide in 1000 ml. of methanol and 93.6 g. of 2-(2-chlorophenyl)-3-(dimethylamino)-2-propenal is refluxed for 16 hours to yield 30.0 g. of a tan solid. The solid is recrystallized from ethanol to yield the product of the Example as white needles, m.p. 252°–254° C.

Additional compounds which may be prepared in a manner similar to that described for the preceding examples are:

1,2-Dihydro-5-(4-fluorophenyl)-2-oxo-3-pyridinecarbonitrile
1,2-Dihydro-5-(2-fluorophenyl)-2-oxo-3-pyridinecarbonitrile
5-(3-Chlorophenyl)-1,2-dihydro-2-oxo-3-pyridinecarbonitrile
5-(4-Bromophenyl)-1,2-dihydro-2-oxo-3-pyridinecarbonitrile
1,2-Dihydro-2-oxo-5-[2-(trifluoromethyl)phenyl]-3-pyridinecarbobonitrile
1,2-Dihydro-2-oxo-5-(3-nitrophenyl)-3-pyridinecarbonitrile
1,2-Dihydro-2-oxo-5-(4-nitrophenyl)-3-pyridinecarbonitrile

EXAMPLE 12

5-(4-Chlorophenyl)-1,2-dihydro-2-oxo-3-pyridinecarboxylic acid

A solution of 10.6 g. of 5-(4-chlorophenyl)-1,2-dihydro-2-oxo-3-pyridinecarbonitrile in 200 ml. of 80% sulfuric acid is heated at reflux temperature for 6 hours. The solution is cooled and poured onto ice, causing a white solid to separate. The solid is collected by filtration and is washed with water to give 9.3 g. of the product of the Example as a white solid, dec. 295° C.

EXAMPLE 13

1,2-Dihydro-5-(3-fluorophenyl)-2-oxo-3-pyridinecarboxylic acid

In the manner described in Example 12, a solution of 59.65 g. of 1,2-dihydro-5-(3-fluorophenyl)-2-oxo-3-pyridinecarbonitrile in 1500 ml. of 80% sulfuric acid is heated at reflux temperature for 6 hours to yield 51.65 g. of the product of the Example as a gray solid.

EXAMPLE 14

1,2-Dihydro-2-oxo-5-(3-methylphenyl)-3-pyridinecarboxylic acid

In the manner described in Example 12, a solution of 10.1 g. of 1,2-dihydro-2-oxo-5-(3-methylphenyl)-3-pyridinecarbonitrile in 150 ml. of 80% sulfuric acid is heated at reflux temperature for 8 hours to yield 5.0 g. of the product of the Example as a gray solid.

EXAMPLE 15

1,2-Dihydro-2-oxo-5-phenyl-3-pyridinecarboxylic acid

In the manner described in Example 12, a solution of 12.5 g. of 1,2-dihydro-2-oxo-5-phenyl-3-pyridinecarbonitrile in 100 ml. of 65% sulfuric acid is heated at reflux temperature for 4 hours. On cooling, yellow crystals are separated. The mixture is poured into water, and the crude product is isolated by filtration and washing with water. The product is dissolved in 5% aqueous sodium hydroxide, filtered through diatomaceous earth and then reacidified with hydrochloric acid to precipitate a white solid. The solid is collected by filtration, washed with water, and is dried to yield 10.9 g. of the product of the example, m.p. 296° C. dec.

The following compounds may also be prepared in a manner similar to that described in Example 12.

1,2-Dihydro-5-(4-fluorophenyl)-2-oxo-3-pyridinecarboxylic acid
1,2-Dihydro-5-(2-fluorophenyl)-2-oxo-3-pyridinecarboxylic acid
5-(3-Chlorophenyl)-1,2-dihydro-2-oxo-3-pyridinecarboxylic acid
5-(4-Bromophenyl)-1,2-dihydro-2-oxo-3-pyridinecarboxylic acid
1,2-Dihydro-5-(3-nitrophenyl)-2-oxo-3-pyridinecarboxylic acid
1,2-Dihydro-5-(4-nitrophenyl)-2-oxo-3-pyridinecarboxylic acid

EXAMPLE 16

1,2-Dihydro-2-oxo-5-phenyl-3-pyridinecarboxylic acid

A mixture of 25.49 g. of 3-amino-2-phenyl-2-propenal and 27.32 g. of dimethyl malonate is reacted with 18.36 g. of sodium methoxide in one liter of methanol. The solution is stirred for 2 hours at room temperature and then is heated at reflux temperature for 3 hours. The resulting mixture is cooled and filtered to collect the precipitate. The solid is suspended in water and acidified with 10% aqueous hydrochloric acid to give a white solid. The solid is collected and washed with water followed by ethanol to yield 18.0 g. of methyl 1,2-dihydro-2-oxo-5-phenyl-3-pyridinecarboxylate. The ester is hydrolyzed by heating at reflux temperature for 2.5 hours in the presence of concentrated hydrochloric acid to give the product of the Example, m.p. 296° C. dec.

EXAMPLE 17

1,2-Dihydro-5-(3-methoxyphenyl)-2-oxo-3-pyridinecarboxylic acid

In the manner described in Example 16 a mixture of 3-amino-2-(3-methoxyphenyl)-2-propenal, dimethyl malonate and sodium methoxide in methanol is refluxed for 3 hours to give methyl, 1,2-dihydro-5-(3-methoxyphenyl)-2-oxo-3-pyridinecarboxylate.

A mixture of the ester and concentrated hydrochloric acid is refluxed for 2.5 hours to give the product of the Example.

EXAMPLE 18

1,2-Dihydro-2-oxo-5-[3-(trifluoromethyl)phenyl]-3-pyridinecarboxylic acid

A mixture of 1.32 g. of 1,2-dihydro-2-oxo-5-[3-(trifluoromethyl)phenyl]-3-pyridinecarbonitrile and 140 ml. of 1:1 concentrated hydrochloric acid and glacial acetic acid is heated at reflux temperature for 16 hours. A white solid is separated which is collected by filtration and is washed with water and ethanol to give 1.05 g. of the product of the Example m.p. 295°–298° C. dec.

EXAMPLE 19

5-(2-Chlorophenyl)-1,2-dihydro-2-oxo-3-pyridinecarboxylic acid

A mixture of 19.0 g. of 5-(2-chlorophenyl)-1,2-dihydro-2-oxo-3-pyridinecarbonitrile and 1:1 concentrated hydrochloric acid and glacial acetic acid is heated at reflux temperature for 16 hours. A yellow solid is separated which is collected by filtration and is washed with water to give 18.4 g. of the product of the Example as yellow needles, m.p. 299°–303° C.

Additional compounds which may be prepared in a manner similar to that described for the preceding Examples are:

1,2-Dihydro-5-(4-methoxyphenyl)-2-oxo-3-pyridinecarboxylic acid
1,2-Dihydro-5-(4-methylphenyl)-2-oxo-3-pyridinecarboxylic acid
1,2-Dihydro-5-(2-methylphenyl)-2-oxo-3-pyridinecarboxylic acid
1,2-Dihydro-5-(3-methylphenyl)-2-oxo-3-pyridinecarboxylic acid
1,2-Dihydro-2-oxo-5-[3-(trifluoromethyl)phenyl]-3-pyridinecarboxylic acid
1,2-Dihydro-2-oxo-5-[4-(trifluoromethyl)phenyl]-3-pyridinecarboxylic acid

EXAMPLE 20

5-(4-Chlorophenyl)-2-(1H)-pyridinone

A mixture of 40.0 g. of 5-(4-chlorophenyl)-1,2-dihydro-2-oxo-3-pyridinecarboxylic acid (prepared as described in Example 12) and 120 ml. of quinoline is heated at reflux temperature for 4 hours. The mixture is cooled and filtered. The solid is washed with ether and then is dissolved in chloroform. The chloroform solution is treated with activated charcoal and is filtered. The filtrate is concentrated and diluted with hexane yielding 22.0 g. of the product of the Example as a tan solid. The solid is recrystallized from chloroform-hexane to give tan crystals, m.p. 183°–185.5° C.

EXAMPLE 21

5-(3-Fluorophenyl)-2(1H)-pyridinone

In the manner described in Example 20, a mixture of 47.5 g. of 1,2-dihydro-5-(3-fluorophenyl)-2-oxo-3-pyridinecarboxylic acid and 200 ml. of quinoline yields 17.15 g. of the product of the Example as a tan solid, m.p. 171°–176° C.

EXAMPLE 22

5-Phenyl-2(1H)-pyridinone

In the manner described in Example 20, a mixture of 12.4 g. of 1,2-dihydro-2-oxo-5-phenyl-3-pyridinecarboxylic acid (prepared as described in Example 15) and 50 ml. of quinoline yields 8.8 g. of the product of the Example as a gray solid, m.p. 173°–177° C.

EXAMPLE 23

5-(3-Methoxyphenyl)-2(1H)-pyridinone

In the manner described in Example 20, heating 1,2-dihydro-5-(3-methoxyphenyl)-2-oxo-3-pyridinecarboxylic acid in quinoline provides the product of the Example.

EXAMPLE 24

5-[3-(trifluoromethyl)phenyl]-2(1H)-pyridinone

In the manner described in Example 20, a mixture of 12.45 g. of 1,2-dihydro-2-oxo-5-[3-(trifluoromethyl)phenyl]-3-pyridinecarboxylic acid and 40 ml. of quinoline yields 6.45 g. of the product of the Example as cream colored crystals, m.p. 171°–176.5° C.

EXAMPLE 25

5-(2-Chlorophenyl)-2(1H)-pyridinone

In the manner described in Example 20, a mixture of 18.0 g. of 5-(2-chlorophenyl)-1,2-dihydro-2-oxo-3-pyridinecarboxylic acid and 75 ml. of quinoline yields 12.3 g. of the product of the Example as tan crystals, m.p. 157°–160° C.

Additional compounds which may be prepared in a manner similar to that described above, are:

5-(4-Fluorophenyl)-2(1H)-pyridinone
5-(2-Fluorophenyl)-2(1H)-pyridinone
5-(3-Chlorophenyl)-2(1H)-pyridinone
5-(4-Bromophenyl)-2(1H)-pyridinone
5-[2-(Trifluoromethyl)phenyl]-2(1H)-pyridinone
5-(3-Nitrophenyl)-2(1H)-pyridinone
5-(4-Nitrophenyl)-2(1H)-pyridinone
5-(4-Methoxyphenyl)-2(1H)-pyridinone
5-(4-Methylphenyl)-2(1H)-pyridinone
5-(2-Methylphenyl)-2(1H)-pyridinone
5-(3-Methylphenyl)-2(1H)-pyridinone
5-(4-tert-Butylphenyl)-2(1H)-pyridinone

EXAMPLE 26

2-Chloro-5-(4-chlorophenyl)pyridine

A mixture of 22.27 g. of 5-(4-chlorophenyl)-2(1H)-pyridinone and 100 ml. of phosphorus oxychloride is refluxed for 16 hours, chilled and poured onto cracked ice. The solid formed is collected by filtration and then is dissolved in chloroform. The chloroform solution is washed with water and with saturated sodium bicarbonate and then is dried over magnesium sulfate. The solvent is evaporated at reduced pressure to yield 21.1 g. of the product of the Example as a gray solid, m.p. 113°–115° C.

EXAMPLE 27

2-Chloro-5-(3-fluorophenyl)pyridine

In the manner described in Example 26, a mixture of 14.39 g. of 5-(3-fluorophenyl)-2(1H)-pyridinone and phosphorus oxychloride provides 11.0 g. of the product of the Example as a tan solid.

EXAMPLE 28

2-Chloro-5-[3-(trifluoromethyl)phenyl]pyridine

In the manner described in Example 26, a mixture of 29.35 g. of 5-[3-(trifluoromethyl)phenyl]-2(1H)-pyridinone and phosphorus oxychloride yields 28.3 g. of the product of the Example as pale yellow crystals, m.p. 40°–42° C.

EXAMPLE 29

2-Chloro-5-(2-chlorophenyl)pyridine

In the manner described in Example 26, a mixture of 11.8 g. of 5-(2-chlorophenyl)-2(1H)-pyridinone and phosphorus oxychloride yields 11.6 g. of the product of the Example as a cream colored solid, m.p. 103°–105.5° C.

EXAMPLE 30

2-Chloro-5-(3-methoxyphenyl)pyridine

In the manner described in Example 26, a mixture of 5-(3-methoxyphenyl)-2(1H)-pyridinone and phosphorus oxychloride yields the product of the Example.

Additional compounds which may be prepared in a manner similar to that described above are:

2-Chloro-5-(4-fluorophenyl)pyridine
2-Chloro-5-(2-fluorophenyl)pyridine

2-Chloro-5-(3-chlorophenyl)pyridine
2-Chloro-5-(4-bromophenyl)pyridine
2-Chloro-5-[2-(trifluoromethyl)phenyl]pyridine
2-Chloro-5-(3-nitrophenyl)pyridine
2-Chloro-5-(4-nitrophenyl)pyridine
2-Chloro-5-(4-methoxyphenyl)pyridine
2-Chloro-5-(4-methylphenyl)pyridine
2-Chloro-5-(2-methylphenyl)pyridine
2-Chloro-5-(3-methylphenyl)pyridine
2-Chloro-5-(4-tert-butylphenyl)pyridine

EXAMPLE 31

5-(4-Chlorophenyl)-2-hydrazinopyridine

A mixture of 21.1 g. of 2-chloro-5-(4-chlorophenyl)-pyridine and 19.5 g. of 95% hydrazine in 200 ml. of pyridine is heated at reflux temperature for 48 hours. The reaction mixture is cooled, poured into an ice-water mixture and filtered. The solid is collected, washed with water and air dried to yield 17.0 g. of the product of the Example as a tan solid.

EXAMPLE 32

2-Hydrazino-5-phenylpyridine

In the manner described in Example 31, a mixture of 4.3 g. of 2-chloro-5-phenylpyridine and 95% hydrazine in pyridine yields 2.0 g. of the product of the Example as a yellow brown solid.

EXAMPLE 33

5-(3-Fluorophenyl)-2-hydrazinopyridine

In the manner described in Example 31, a mixture of 11.0 g. of 2-chloro-5-(3-fluorophenyl)pyridine and 95% hydrazine in pyridine yields 6.0 g. of the product of the Example as tan plates.

EXAMPLE 34

2-Hydrazino-5-[3-(trifluoromethyl)phenyl]pyridine

In the manner described in Example 31, a mixture of 5.15 g. of 2-chloro-5-[3-trifluoromethyl)phenyl]pyridine and 95% hydrazine in pyridine provides 3.95 g. of the product of the Example as a tan solid, m.p. 84°–87° C.

EXAMPLE 35

5-(2-Chlorophenyl)-2-hydrazinopyridine

In the manner described in Example 31, a mixture of 10.97 g. of 2-chloro-5-(2-chlorophenyl)pyridine and 95% hydrazine in pyridine yields 9.43 g. of the product of the Example as a cream colored solid, m.p. 139°–140.5° C.

EXAMPLE 36

2-Hydrazino-5-(3-methoxyphenyl)pyridine

In the manner described in Example 31, a mixture of 2-chloro-5-(3-methoxyphenyl)pyridine and hydrazine yields the product of the Example.

Additional compounds which may be prepared in a manner similar to that described above are:

5-(4-Fluorophenyl)-2-hydrazinopyridine
5-(2-Fluorophenyl)-2-hydrazinopyridine
5-(3-Chlorophenyl)-2-hydrazinopyridine
5-(4-Bromophenyl)-2-hydrazinopyridine
2-Hydrazino-5-[2-(trifluoromethyl)phenyl]pyridine
2-Hydrazino-5-(3-nitrophenyl)pyridine
2-Hydrazino-5-(4-nitrophenyl)pyridine
2-Hydrazino-5-(4-methoxyphenyl)pyridine
2-Hydrazino-5-(4-methylphenyl)pyridine
2-Hydrazino-5-(2-methylphenyl)pyridine
2-Hydrazino-5-(3-methylphenyl)pyridine
2-Hydrazino-5-(4-tert-butylphenyl)pyridine

EXAMPLE 37

6-(4-Chlorophenyl)-3-methyl-1,2,4-triazolo[4,3-a]pyridine

A mixture of 8.5 g. of 5-(4-chlorophenyl)-2-hydrazinopyridine and 80 ml. of ethyl orthoacetate is refluxed for 5 hours, the mixture is filtered and the solid is washed with hexane to afford 5.0 g. of the product of the Example as a tan solid, m.p. 192°–193.5° C.

EXAMPLE 38

6-(3-Fluorophenyl)-3-methyl-1,2,4-triazolo[4,3-a]pyridine

In the manner described in Example 37, a mixture of 3.0 g. of 5-(3-fluorophenyl)-2-hydrazinopyridine and 30 ml. of ethyl orthoacetate yields 2.15 g. of the product of the Example as a tan solid, m.p. 179°–182° C.

EXAMPLE 39

3-Methyl-6-phenyl-1,2,4-triazolo[4,3-a]pyridine

In the manner described in Example 37, a mixture of 0.85 g. of 2-hydrazino-5-phenylpyridine and 10 ml. of ethyl orthoacetate yields 0.55 g. of the product of the Example as pale yellow plates, m.p. 182°–184° C.

EXAMPLE 40

3-Methyl-6-[3-(trifluoromethyl)phenyl]-1,2,4-triazolo[4,3-a]pyridine

In the manner described in Example 37, a mixture of 1.15 g. of 2-hydrazino-5-[3-(trifluoromethyl)phenyl]-pyridine and 15 ml. of ethyl orthoacetate yields 0.507 g. of the product of the Example as yellow-green crystals m.p. 185°–187° C.

EXAMPLE 41

6-(2-Chlorophenyl)-3-methyl-1,2,4-triazolo[4,3-a]pyridine

In the manner described in Example 37, a mixture of 1.1 g. of 5-(2-chlorophenyl)-2-hydrazinopyridine and 10 ml. of ethyl orthoacetate yields 0.9 g. of the product of the Example as a tan solid m.p. 175°–177° C.

EXAMPLE 42

6-(3-Methoxyphenyl)-3-methyl-1,2,4-triazolo[4,3-a]pyridine

In the manner described in Example 37, a mixture of 2-hydrazino-5-(3-methoxyphenyl)pyridine and ethyl orthoacetate provides the product of the Example.

Additional compounds which may be prepared in a manner similar to that described above are:

6-(4-Fluorophenyl)-3-methyl-1,2,4-triazolo[4,3-a]pyridine
6-(2-Florophenyl)-3-methyl-1,2,4-triazolo[4,3-a]pyridine
6-(3-Chlorophenyl)-3-methyl-1,2,4-triazolo[4,3-a]pyridine
6-(4-Bromophenyl)-3-methyl-1,2,4-triazolo[4,3-a]pyridine 6-[2-(trifluoromethyl)phenyl]-3-methyl-1,2,4-triazolo[4,3-a]pyridine 6-(4-methoxyphenyl)-3-methyl-1,2,4-triazolo[4,3-a]pyridine 3-Methyl-6-(3-nitrophenyl)-1,2,4-triazolo[4,3-a]pyridine 3-Methyl-6-(4-nitrophenyl)-1,2,4-triazolo[4,3-a]pyridine 3-Methyl-6-(4-methylphenyl)-1,2,4-triazolo[4,3-a]pyridine 3-Methyl-6-(2-methylphenyl)-1,2,4-triazolo[4,3-a]pyridine 3,Methyl-6-(3-methylphenyl)-1,2,4-triazolo[4,3-a[pyridine 3-Methyl-6-(4-tert-butylphenyl)-1,2,4-triazolo[4,3-a]pyridine

EXAMPLE 43

1,2-Dihydro-2-oxo-5-phenyl-3-pyridinecarboxylic acid

A 8.4 g. portion of 1,2-dihydro-5-phenyl-2(1H)-oxo-3-pyridinecarboxamide (prepared in a manner similar to that described in Example 9 with the substitution of malonamide for cyanoacetamide) is heated with 150 ml. of 80% aqueous sulfuric acid for 6 hours. The reaction mixture is poured onto cracked ice and chilled to yield 450 mg. of the product of the Example as a gray solid.

EXAMPLE 44

Ethyl 1,2-dihydro-2-oxo-5-[3-(trifluoromethyl)phenyl]-3-pyridinecarboxylate

A solution of sodium ethoxide is prepared by dissolving 0.92 g. of sodium metal in 100 ml. of ethanol. To this solution is added 2.9 g. of ethyl malonomate and 4.86 g. of 3-(dimethylamino)-2-[3-(trifluoromethyl)phenyl]-2-propenal. The resulting mixture is heated at reflux temperature fo 12 hours, then is filtered to remove a yellow solid. The solid is suspended in water and the mixture acidified with hydrochloric acid. The mixture is filtered and the solid is dissolved in methylene chloride. The organic solution is washed with water, dried and evaporated to yield 850 mg. of the product of the Example as a yellow solid, m.p. 159°–160° C.

EXAMPLE 45

1,2-Dihydro-2-oxo-5-[3-(trifluoromethyl)phenyl]-3-pyridinecarboxamide

To a solution of 1.1 g. of malonamide and 1.1 g. of sodium methoxide in 50 ml. of methanol is added 2.43 g. of 3-(dimethylamino)-2-[3-(trifluoromethyl)phenyl]-2-propenal. The resulting mixture is heated at reflux temperature for 12 hours. The mixture is cooled, concentrated and acidified with hydrochloric acid to yield 800 mg. of the product of the Example as a yellow solid m.p. 276.5°–278.5° C.

EXAMPLE 46

α-Formyl-3-(trifluoromethyl)benzeneacetonitrile

To a slurry of 30.0 g. of sodium methoxide in 1200 ml. of toluene and 43.4 g. of ethyl formate is added dropwise with stirring 98.75 g. of 3-(trifluoromethyl)benzeneacetonitrile in 75 ml. of toluene over a 10 minute period. The temperature of the mixture rises to 35° C. and the mixture thickens. Stirring is continued for 2 hours and then one liter of water is added. The aqueous layer is acidified and a precipitate is formed by scratching to give 85.0 g. of the product of the Example as a white solid, m.p. 103°–106.5° C.

EXAMPLE 47

3-Amino-2-[3-(trifluoromethyl)phenyl]-2-propenal

Four 21.0 g. portions of α-formyl-3-(trifluoromethyl)benzeneacetonitrile each in 250 ml. of ethanol are hydrogenated in the presence of 40 g. of Raney Nickel (number 28) at 20 psi pressure until no more hydrogen is absorbed. The resulting mixtures are filtered and the filtrates are combined and passed through 150 g. of alumina (Woelm, activity II) with 1:1 methylene chloride-ethyl acetate. The resulting eluate is concentrated at reduced pressure and the residue triturated with hexane to give 39.4 g. of the product of the Example as a yellow solid, m.p. 63°–70° C.

EXAMPLE 48

Methyl 1,2-dihydro-2-oxo-5-[3-(trifluoromethyl)phenyl]-3-pyridinecarboxylate

To a solution of 1.5 g. of sodium methoxide in 85 ml. of methanol is added 2.25 g. of dimethyl malonate and 2.93 g. of 3-amino-2-[3-(trifluoromethyl)phenyl]-2-propenal. The mixture is stirred at room temperature for 16 hours with precipitation of a yellow solid. The mixture is heated at reflux temperature for 2 hours, cooled and filtered to obtain a white solid. The solid is washed with ether, suspended in water and acidified with hydrochloric acid to yield 1.75 g. of the product of the Example as a white solid, m.p. 195°–201° C.

EXAMPLE 49

α-Formyl-3-methoxybenzeneacetonitrile

In the manner described in Example 46, the reaction of 3-methoxybenzeneacetonitrile with sodium methoxide and ethyl formate provides the product of the Example.

EXAMPLE 50

3-Amino-2-(3-methoxy)phenyl-2-propenal

In the manner described in Example 47, the reduction of α-formyl-3-methoxybenzeneacetonitrile with hydrogen in the presence of Raney nickel provides the product of the Example.

EXAMPLE 51

Methyl 1,2-dihydro-5(3-methoxyphenyl)-2-oxo-3-pyridinecarboxylate

In the manner described in Example 48, the product of Example 50 is reacted with dimethyl malonate and sodium methoxide to give the product of the Example.

EXAMPLE 52

3-Methyl-6-[3-(trifluoromethyl)phenyl]-1,2,4-triazolo[4,3-a]pyridine

A mixture of 2 g. of 2-chloro-5-[3-(trifluoromethyl)phenyl]pyridine and two equivalents of acetylhydrazine in n-butanol is heated at reflux for 48 hours to give the product of the Example as crystals, m.p. 185°–187° C.

EXAMPLE 53

3-Ethyl-6-[3-(trifluoromethyl)phenyl]-1,2,4-triazolo[4,3-a]pyridine

In the manner described in Example 37, a mixture of 1.15 g. of 2-hydrazino-5-[3-(trifluoromethyl)phenyl]- pyridine and 15 ml. of ethyl orthopropionate yields the product of the Example.

Additional compounds which may be prepared in a manner similar to that described above are:

3-Ethyl-6-(4-fluorophenyl)-1,2,4-triazolo[4,3-a]pyridine
3-Ethyl-6-(2-fluorophenyl)-1,2,4-triazolo[4,3-a]pyridine
6-(3-Chlorophenyl)-3-ethyl-1,2,4-triazolo[4,3-a]pyridine
6-(4-Bromophenyl)-3-ethyl-1,2,4-triazolo[4,3-a]pyridine
3-Ethyl-6-[3-(trifluoromethyl)phenyl]-1,2,4-triazolo[4,3-a]pyridine
3-Ethyl-6-(4-methoxyphenyl)-1,2,4-triazolo[4,3-a]pyridine
3-Ethyl-6-(3-nitrophenyl)-1,2,4-triazolo[4,3-a]pyridine
3-Ethyl-6-(4-nitrophenyl)-1,2,4-triazolo[4,3-a]pyridine
3-Ethyl-6-(4-methylphenyl)-1,2,4-triazolo[4,3-a]pyridine
3-Ethyl-6-(2-methylphenyl)-1,2,4-triazolo[4,3-a]pyridine
3-Ethyl-6-(3-methylphenyl)-1,2,4-triazolo[4,3-a]pyridine
3-Ethyl-6-(4-tert-butylphenyl)-1,2,4-triazolo[4,3-a]pyridine

We claim:

1. A compound selected from the group consisting of those of the formula:

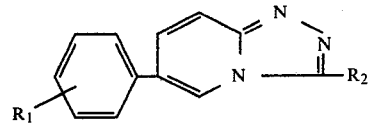

wherein $R_1$ is hydrogen, alkyl ($C_1$–$C_4$), alkoxy ($C_1$–$C_4$), fluoro, chloro, bromo, trifluoromethyl, cyano, carboxy, alkoxycarbonyl ($C_2$–$C_5$), carboxamido, nitro, amino, acetylamino, monoalkylamino ($C_1$–$C_4$) or dialkylamino wherein each alkyl group has up to 4 carbon atoms and $R_2$ is alkyl ($C_1$–$C_3$); and the pharmacologically acceptable acid-addition salts thereof.

2. The compound according to claim 1, 6-(4-chlorophenyl)-3-methyl-1,2,4-triazolo[4,3-a]pyridine.

3. The compound according to claim 1, 6-(3-fluorophenyl)-3-methyl-1,2,4-triazolo[4,3-a]pyridine.

4. The compound according to claim 1, 3-methyl-6-[3-(trifluoromethyl)phenyl]-1,2,4-triazolo[4,3-a]pyridine.

5. The compound according to claim 1, 3-methyl-6-phenyl-1,2,4-triazolo[4,3-a]pyridine.

6. The compound according to claim 1, 6-(3-methoxyphenyl)-3-methyl-1,2,4-triazolo[4,3-a]pyridine.

7. The compound according to claim 1, 6-(4-fluorophenyl)-3-methyl-1,2,4-triazolo[4,3-a]pyridine.

* * * * *